United States Patent
Lin et al.

(10) Patent No.: US 6,862,919 B2
(45) Date of Patent: Mar. 8, 2005

(54) ETHANOL AND VOLATILITY SENSOR AND FABRICATION METHOD

(75) Inventors: Yingjie Lin, El Paso, TX (US); Da Yu Wang, Troy, MI (US); Robert Jerome Farhat, Grosse Point Park, MI (US); Raymond L. Bloink, Swartz Creek, MI (US); William J. LaBarge, Bay City, MI (US)

(73) Assignee: Delphi Technologies, Inc., Troy, MI (US)

( * ) Notice: Subject to any disclaimer, the term of this patent is extended or adjusted under 35 U.S.C. 154(b) by 129 days.

(21) Appl. No.: 10/464,337

(22) Filed: Jun. 17, 2003

(65) Prior Publication Data

US 2004/0255647 A1 Dec. 23, 2004

(51) Int. Cl.[7] ............................................... G01N 11/00
(52) U.S. Cl. .................. 73/53.01; 73/53.06; 73/304 C; 73/290 R
(58) Field of Search .............................. 73/53.01, 53.06, 73/290 R, 304 C, 23.31, 23.32, 31.05, 31.06, 31.07

(56) References Cited

U.S. PATENT DOCUMENTS

| | | |
|---|---|---|
| 4,702,107 A | 10/1987 | Guerrini et al. |
| 4,779,460 A | 10/1988 | Cruickshank |
| RE32,925 E | 5/1989 | Chen et al. |
| 4,923,770 A | 5/1990 | Grasselli et al. |
| 5,267,475 A | 12/1993 | Gaston |
| 5,740,854 A | 4/1998 | Inoue et al. |
| 5,743,136 A | 4/1998 | Gaston et al. |
| 5,746,088 A | 5/1998 | Sawert et al. |
| 5,882,736 A | 3/1999 | Stein et al. |
| 5,897,965 A | 4/1999 | Itoh et al. |
| 6,021,668 A | 2/2000 | Sawert et al. |
| 6,083,570 A | 7/2000 | Lemelson et al. |
| 6,564,624 B2 | 5/2003 | Lin et al. ................... 73/118.1 |
| 6,588,253 B2 | 7/2003 | Lambert et al. .......... 73/53.01 |
| 6,634,210 B1 * | 10/2003 | Bosch et al. ............... 73/23.33 |
| 2003/0033858 A1 * | 2/2003 | Lambert et al. .......... 73/53.01 |

OTHER PUBLICATIONS

E.F. Smith, III and Hugh W. Ireland, "Design Guidelines for Automotive Fuel Level Sensors", Society of Automotive Engineers, Inc. (2002).

Pelletier et al., "Mechanical Properties of Amorphous Metallic Materials: Viscoelasticity and Viscosity", Science of Metastable and Nanocrystalline Alloys Structure, Properties and Modelling, Denmark 2001. (Abstract).

Nishiyama et al., "Flux treated Pd–Cu–Ni–P amorphous alloy having low critical cooling rate", Materials Transactions, JIM, v 38, n 5, May, 1997, p 464–472. (Abstract).

Schroers et al., "Crystallization of bulk glass forming Pd-based melts", Materials Science Forum, v 360–362, 2001, Metastable, Mechanically Alloyed and Nanocrystalline Materials (ISMANAM 2000), Jul. 9–14, 2000, Oxford, p 79–84. (Abstract).

(List continued on next page.)

*Primary Examiner*—Hezron Williams
*Assistant Examiner*—Rodney Frank
(74) *Attorney, Agent, or Firm*—Jimmy L. Funke

(57) ABSTRACT

In one embodiment, a method for forming the sensor comprises: disposing capacitance electrodes and a heater on green layers; disposing the layers such that the capacitance electrodes are disposed between adjacent green layers and the heater is disposed on a side of a green layer opposite one of the capacitance electrodes; disposing a gap insert in physical contact with the capacitance electrodes, wherein the gap insert has a higher sintering temperature than the green layers; sintering the green layers; and removing the gap insert.

28 Claims, 4 Drawing Sheets

OTHER PUBLICATIONS

Lambert et al., "Study of electroless nickel coatings containing low phosphorus", Thin Solid Films, v 177, n 1–2, Oct., 1989, p 207–223. (Abatract).

Dian et al., "Chemical interaction at the Pd–B interface", Journal of Magnetism and Magnetic Materials, v 126, n 1–3, Sep., 1993., Proceedings of the 1st International Symposium on Metallic Multilayers, Mar. 1–5, 1993, Kyoto, Jpn, p 25–27. (Abstract).

Liao et al., "B–Pd (boron–palladium) system", Journal of Phase Equilibria, v17, Aug. 4, 1996, P 340–346. (Abstract).

Beck et al., Unit cell parameters densities of the solid solution Pd(B), Materials Science Forum, v321 (II, 2000, Proceedings of the 1998 6th European Powder Diffraction Conference (EPDIC 6), Aug. 22–Aug. 25, 1998, Budapest, Hung, p 604–609. (Abstract).

Boonekamp et al., "Selective metallization of silicon surfaces the adsorption of sterically stabilized palladium particles on H–terminated Si(100), Si3N4, and SiO2", Journal of the Electrochemical Society, v142, Feb. 2, 1995, p 519–524. (Abstract).

Kawashima et al., "Structure and corresion behavior of electro–deposited Ni–P alloys", Corrosion Engineering, v 38, n 11, 1989, p 643–653. (Abstract).

Ivanov, MV, "Electroless nickel–boron–phosphorus coatings: Protective and functional properties", Protection of Metals, 37(6): 592–596 Nov.–Dec. 2001. (Abstract).

Japanese Abstract for JP7118866.

B. M. Mohamed et al., "Kinetics and mechanism of formation of tricalcium aluminate, Ca3A12O6", Thermochimica Acta 6944 (2002) 1–10.

http://www.metglas.com/product/pages (3 pages).

Onoda et al., "Mechanism of boron codeposition in electrodeposited Ni–B alloy films and calaculation of the amount of codeposited boron", Transactions of the Institute of Metal Finishing, 77: 44–48 Part 1 Jan. 1999. (Abstract).

Tsai et al., "Thermal stability and mechanical properties of Ni–W–P electroless deposits", Surface and Coatings Technology, 146: 502–507 Sep.–Oct. 2001. (Abstract).

Ashassi–Sorkhabi et al., "Electroless deposition of Ni–Cu–P alloy and study of the influences of some parameters on the properties of deposits", Applied Surface Science, 185 (3–4): 155–160 Jan. 15, 2002 (Abstract).

Yi et al., "The effects of the concentration of individual reactants on Fe–Ni–P–B nanoparticles fabricated by chemical reduction", Journal of Materials Processing Technology, 117 (1–2): 37–42 Nov. 2, 2001. (Abstract).

Wayne D. Rupert, "Brazing with copper phosphorus alloys", Refrigeration Service & Contracting, v 65, n 1, Jan., 1997 p 54–57. (Abstract).

Richard E. Ballentine, "Silver's role in phosphorus–copper brazing filler metals", Welding Journal (Miami, Fla), v 73, n 10, Oct., 1994, p 41–42 (Abstract).

Willnecker et al., "Undercooling investigations and heat capacity measurements on Pd–Ni–P melts", Journal of Non–Crystalline Solids, v 156–58, pt 1, May 2, 1993. (Abstract).

Alamgir et al., "X–ray photoelectron spectroscopy analysis of bulk Pd–Ni–P metallic glasses", Philosophical Magazine B: Physics of Condensed Matter; Statistical Mechanics, Electronic, Optical and Magnetic Properties, v 79, n 2, Feb., 1999, p 239–247. (Abstract).

He et al., "Synthesis and properties of bulk metallic glasses in Pd–Ni–P and Pd–Cu–P alloys", Materials Research Society Symposium Proceedings, v 455, 1997, Structure and Dynamics of Glasses and Glass Formers, Proceedings of the 1996 MRS Fall Meeting, Dec. 2–6, 1996, Boston, MA, USA, P 495–500. (Abstract).

Lee et al., "Effect of phosphorus addition on the corrosion behavior of amorphous Ni–30Ta–P alloys in 12 M HC1", Corrosion Science, v37, Feb. 2, 1995, p 321–330 (Abstract).

Lee et al., "Effect phosphorus addition on the corrosion behavior of are–melted Ni–10Ta–P alloys in 12 M HCI", Corrosion Science, v38, Mar. 3, 1996, p 469–485 (Abstract).

U.S. Appl. No. 10/146,743, filed May 16, 2002.

U.S. Appl. No. 10/150,675, filed May 17, 2002.

U.S. Appl. No. 10/117,833, filed Apr. 8, 2002.

http://www.memagazine.org/backissues/june98/features/metallic/metallic.html "Metallic Glasses Bulk Up"(6 pages).

http://www.macindustrialproducts.com/entypes.html "EN Types" (2 pages).

* cited by examiner

ETHANOL AND VOLATILITY SENSOR AND FABRICATION METHOD

BACKGROUND OF THE INVENTION

It is highly desirable in the automotive industry to reduce pollutants emitted from an engine's exhaust. One way of achieving this goal is by means of a sensor, which can detect both the ethanol concentration and the volatility level of a particular fuel. By detecting these two variables, the engine can use a pre-programmed "look-up table" to select the best operation parameters, e.g., air/fuel ratios, timing of ignition start-up, etc., to generate a minimum amount of exhaust pollutants.

The sensor detects the fuel's ethanol concentration by determining the fuel's initial capacitance after first entering the sensor. The heater, which is attached to the sensor, then monotonically increases the sensor's temperature until most of the trapped fuel (e.g., greater than 80 wt %) is fully evaporated. As the fuel is evaporated, the fuel sample amount changes (the changes in capacitance) with the fuel temperature changes are detected by the sensor and are indicative of the fuel's volatility.

These sensors, however, have several drawbacks. First, the sensors comprise a large number of components, which increases the manufacturing costs of the sensors. Second, the sensors tend to be formed, at least in part, with glues, pastes, and other adhesives. As the fuels to which the sensors are exposed are solvents, they tend to destroy the glues and debond the heater and temperature sensor from the capacitance sensor. Third, the sensor is susceptible to thermal cycle fatigue as the thermal cycles, by which the sensor achieves its function, tend to destroy the glues holding the capacitance sensor to the temperature sensor and to the heater.

SUMMARY OF THE INVENTION

Disclosed herein is a sensor and methods for making and using the same. In one embodiment, the sensor comprises a monolithic structure comprising a first capacitance electrode in fluid communication with a second capacitance electrode through a gap in fluid communication with an exterior of the sensor; a first layer disposed on a side of the first capacitance electrode opposite the second capacitance electrode; a first heater disposed between a third layer and the first layer; a second layer disposed on a side of the second capacitance electrode opposite the first capacitance electrode; and a second heater disposed between a fourth layer and the second layer.

In one embodiment, the method for forming the sensor comprises: disposing capacitance electrodes and a heater on green layers; disposing the layers such that the capacitance electrodes are disposed between adjacent green layers and the heater is disposed on a side of a green layer opposite one of the capacitance electrodes; disposing a gap insert in physical contact with the capacitance electrodes, wherein the gap insert has a higher sintering temperature than the green layers; sintering the green layers; and removing the gap insert.

The above-described and other features will be appreciated and understood by those skilled in the art from the following detailed description, drawings, and appended claims.

BRIEF DESCRIPTION OF THE DRAWINGS

Referring now to the figures wherein the like elements are numbered alike.

DESCRIPTION OF THE PREFERRED EMBODIMENT

Figures 1, 2:
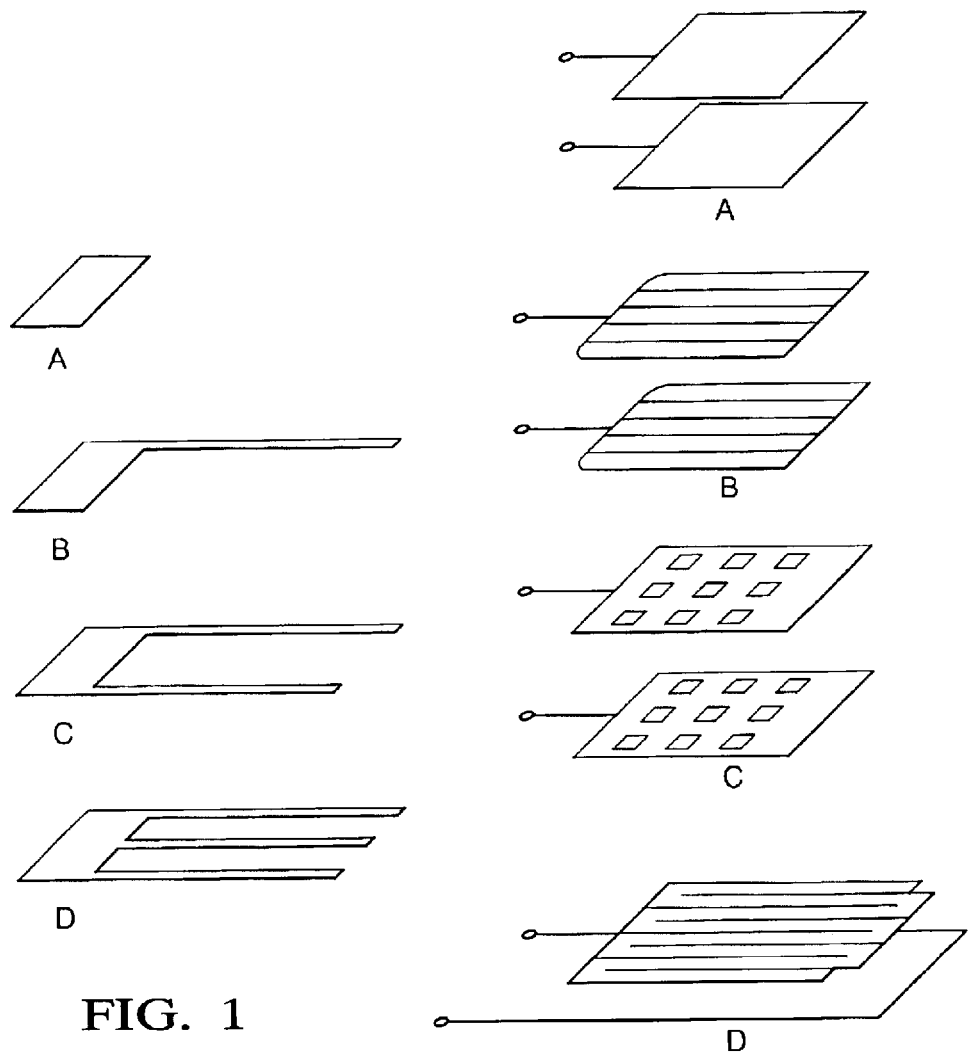
FIGS. 1A–D are schematics depicting exemplary geometrical configurations for the base insert.
FIGS. 2A–D are schematics depicting exemplary geometrical configurations for the capacitance electrodes.

Disclosed herein are a sensor and its method of manufacture. More particularly, disclosed herein is a monolithic volatility sensor. The method for making the sensor comprises disposing a base insert between the capacitance electrodes and co-firing the sensor to densify the layers. The gap insert comprises a material having a higher sintering temperature than layers on which the electrodes are disposed. As a result, the electrode layers can be sintered while a gap is maintained between the electrodes. Once the sensor is sintered the gap insert is removed, thereby the base insert and the two capacitance electrodes form a gap space in which fuel may be measured for volatility and ethanol concentration. The sensor comprises a plurality of layers comprising opposing capacitance electrodes, a gap disposed between and in fluid communication with the capacitance electrodes and the exterior of the sensor, heater(s) disposed on layers located on sides of the capacitance electrode layers opposite the gap (optionally a single heater disposed on the side of one of the capacitance electrodes opposite the other capacitance electrode, with at least two heaters preferred), and optionally guard electrodes and temperature detectors disposed on layers between the heaters and the capacitance electrodes.

Since the sensor is cofired, in order to maintain a desired gap between adjacent capacitance electrodes, a gap insert (attention: we have base insert and gap insert. The gap insert will be taken away to leave a gap, to the end of sensor fabrication. The base insert is to hold the sensor together at the end of the sensor fabrication and is sintered monolithically together with the rest of the sensor body) having a higher sintering temperature than the layers supporting the capacitance electrodes is needed. This gap insert maintains a gap between these electrodes of a desired size and geometry. After sintering, the gap insert can be easily taken out (physically by removing, or using liquid to wash away, or using liquid together with ultrasonic vibration to wash away the insert) and leave a gap behind. The gap formed between the electrodes is capable of holding fuel. As such, the size of the gap is preferably such that the capillary force resulting along the wall of the major plates can hold the fuel. Therefore, the thickness (d) and height (h) of the gap may be governed by the formula:

$$dh < \frac{\left(\frac{2(A)}{G}\right)}{D}$$

where d is the gap width, h is the height of the gap that is vertical to the ground plane, A is the surface energy loss (per unit surface area) created by replacing air with fuel, G is the acceleration of gravity at the surface of the earth, and D is the fuel's liquid density.

Taking this into consideration, in one embodiment, the gap may be about 0.1 millimeter (mm) to about 0.6 mm thick. Within this range, a thickness of greater than or equal to about 0.2 mm is preferred, and greater than or equal to about 0.4 mm particularly preferred. Also within this range, a gap height of less than or equal to about 10 mm is preferred, with less than or equal to about 6 mm more preferred, and less than or equal to about 4.5 mm particularly preferred. Additionally, the gap may be about 0.2 mm to about 20 mm long. Within this range, a length of greater than or equal to about 2 mm is preferred, with greater than or equal to about 4 mm more preferred, and greater than or equal to about 6 mm especially preferred. Also within this range, a length of less than or equal to about 20 mm is preferred, with less than or equal to about 10 mm more preferred, and less than or equal to about 6 mm especially preferred.

The geometry of the base insert, and hence the gap, is sufficient to enable operable communication between the capacitance electrodes such that the desired ethanol concentration and/or fuel volatility can be determined, to enable the gap insert to be removed once the sensor has been sintered, and to enable ingress of the fluid to be sensed (e.g., fuel). Consequently, the gap insert is typically disposed at one end of the sensor, the proximal end, and extends a sufficient distance toward the opposite end, i.e., the distal end, to enable physical contact between the base insert and each of the capacitance electrodes. In other words, the gap insert has a geometry sufficient to form a gap having fluid communication with both capacitance electrodes and the exterior of the sensor. The shape of a base insert will determine the shape of the gap. The base insert is an insert that holds the part of sensor on the two sides of the gap together. The base insert is sintered, monolithically, with the rest of the sensor except the gap insert; i.e., the base insert and green layers, once sintered from one single piece of ceramic. The gap insert does not sinter and will be taken away physically after the sintering to create a gap between the capacitance electrodes. The base insert and the gap insert together form a physical layer which can be laminated thermally with the rest of the sensor at green stage. After sintering, the base insert will remain with the rest of the sensor and the gap insert will be removed to form a gap for holding liquid (e.g., fuel).

For example, referring to FIG. 1, the base insert may comprise a quadrilateral element (FIG. 1a), a quadrilateral element having one lateral extension extending from a top portion of the quadrilateral element (FIG. 1b), a quadrilateral element having two lateral extensions with one extending from a top portion and the other extending from a bottom portion of the quadrilateral element (FIG. 1c), and a quadrilateral clement having a lateral extension extending from a top portion, a lateral extension extending from a bottom portion, and a lateral extension extending from a middle portion of the quadrilateral element (FIG. 1d). Additional lateral extensions may be physically connected to the quadrilateral element resulting in a base insert having multiple lateral extensions.

The base insert illustrated in FIG. 1A is the simplest shape to fabricate, the remaining illustrated embodiments of the inserts (B, C, and D) have more complex shapes because of the quadrilateral element(s). The purpose of the quadrilateral element(s) is to increase the mechanical integrity of the sensor device. In some cases, quadrilateral elements can be used to hold the gap in position mechanically, without sagging, during the sintering stage if there is no gap insert in place. However, since the existence of the quadrilateral elements occupies a portion of the area that would have been gap space (thereby diminishing the volume available to hold liquid), and due to a resulting decrease in the signal strength during use, the preferred shape of the base insert is the one illustrated in FIG. 1A.

Since the gap insert maintains a space between the capacitance electrodes during sintering, the gap insert has a sintering temperature greater than the sintering temperature of the rest sensor layers. In order to allow for inaccuracies in the sintering process and equipment, the base insert preferably has a sintering temperature greater than or equal to about 200° C. greater than the sintering temperature of the layers, with a sintering temperature greater than or equal to about 300° C. greater than the sintering temperature of the layers more preferred, and a sintering temperature greater than or equal to about 500° C. greater than the sintering temperature of the layers especially preferred.

Due to the function of the gap insert, the material employed therefore is dependent upon the material employed for the rest of the sensor layers. The sensor layers (excluding the gap insert) can comprise a material that is capable of inhibiting electrical communication between various layers, providing physical protection and structural integrity to the components disposed on the layers, and capable of sintering at a desired sintering temperature. Although the materials for each layer is preferably the same, different material having substantially similar coefficients of thermal expansion, shrinkage characteristics, and chemical compatibility can be employed as long as they can be sintered monolithically. To enable sintering at a low sintering temperature (e.g., less than or equal to about 900° C.), the material can be an alumina compound such as aluminum oxide and a material having a lower sintering temperature than the aluminum oxide (e.g., a sintering agent from Group 1 or 2 of the Periodic Table of Elements). Alternative possible high temperature materials other than aluminum oxide include zirconium oxide, yttrium oxide, lanthanum oxide, silicon oxide, and the like, as well as combinations comprising at least one of any of the above mentioned materials.

Sintering agents, such as low melting temperature glass (i.e., melted below the firing temperature, e.g., less than 1,500° C.), for example, formed from low temperature melting Groups 1 and 2 elements (such as lithium, magnesium,: sodium, potassium, barium, and the like) and high temperature melting oxides (such as alumina, silica, and the like). Preferably, the melting temperature of the sintering agent is less than 1,500° C., with less than or equal to about 1,450° C. more preferred, less: than or equal to about 1,350° C. even more preferred, and less than or equal to about 1,250° C. especially preferred. Examples of sintering agents include: glass frits, such as a lithium oxide-aluminum oxide-silicon oxide ($Li_2O$—$Al_2O_3$—$SiO_2$) system, a magnesium oxide-aluminum oxide-silicon oxide ($MgO$—$Al_2O_3$—$SiO_2$) system, a sodium oxide-aluminum oxide-silicon oxide ($Na_2O$—$Al_2O_3$—$SiO_2$), a barium oxide-aluminum oxide-silicon oxide ($BaO$—$Al_2O_3$—$SiO_2$) system, a lithium oxide-magnesium oxide-aluminum oxide-silicon oxide ($Li_2O$—$MgO$—$Al_2O_3$—$SiO_2$) system, a potassium oxide-magnesium oxide-aluminum oxide-silicon oxide ($K_2O$—$MgO$—$Al_2O_3$—$SiO_2$) system, and the like, as well as combinations comprising at least one of the foregoing sintering agents. Without the sintering agents, firing is typically at about 1,500° C. With the sintering agents firing may be done at temperatures of about 750° C. to about 900°

C., depending upon the specific type and amount of sintering agents employed.

When an aluminum oxide compound is employed for the gap insert, pure aluminum oxide (e.g., aluminum oxide having a purity of greater than or equal to about 99.7 weight percent (wt %) based upon the total weight of the aluminum oxide), or an aluminum oxide having a lower concentration of sintering agent such that the desired delta in sintering temperatures is attained.

The gap insert may include a wide variety of geometrical shapes including, but not limited to, rounded (e.g., round, oval, elliptical, irregular, and the like), polygonal (e.g., triangular, square, trapezoidal, pentagonal, hexagonal, heptagonal, octagonal, tapered, and the like), and the like, as well as combinations comprising at least one of the foregoing geometries.

Disposed on at least one layer adjacent the base insert and the gap insert are capacitance electrodes. These electrodes, which can be disposed on the same or different layers, are not in physical contact with one another, with electrical communication therebetween created by fuel when it is disposed in the gap. The capacitance electrodes may be any geometrical shape and dimension complementary to the layers such that each capacitance electrode covers substantially all (e.g., less than or equal to about 98% of the surface of a layer) or a portion of the layer. Exemplary geometrical configurations for the capacitance electrodes are shown in FIGS. 2A–D. The capacitance electrodes may be disposed over the entire surface area of the layer (FIG. 2A), and therefore may take the geometrical shape of the layer. The electrodes may be formed around holes, as shown in FIG. 2C. Alternatively, the capacitance electrodes may form thin strips disposed on two different layers (FIG. 2B) or the same layer (FIG. 2D). The creation of holes, gaps between strips as shown in FIG. b–d are to reduce the amount of electrode materials used for capacitance measurement. This approach can save the amount of precious metal usage if precious metals or alloys are used as the capacitance electrode materials, while sacrifice of the alternating current (AC) capacitance signal strength will be minimal.

Each capacitance electrode, which comprises the same or a different material than the other electrodes, may comprise any material capable of obtaining the desired sensor reading. Some possible metals include: cobalt (Co), rhodium (Rh), iridium (Ir), nickel (Ni), palladium (Pd), platinum (Pt), iridium (Ir), copper (Cu), silver (Ag), gold (Au), zinc (Zn), aluminum (Al), tin (Sn), lead (Pb), yttrium (Y), lanthanum (La), zirconium (Zr), titanium (Ti), hafnium (Hf), and the like, as well as, oxides, cermets, alloys, and combinations comprising one of the foregoing metals. For use as an ethanol and/or volatility sensor, the capacitance electrode(s) preferably comprises gold and/or a mixed alloy such as Pd—Cu—Ni—P or Pd—Cu—Ni—Zn—P, which is preferred for durability and cost efficiency.

Alternatively or in addition, the capacitance electrodes may comprise an amorphous metal material (e.g., a glassy metal) comprising elements from Groups 4, 9, 10, 11, 12, 13, and phosphorous and/or boron. As used herein, amorphous metal materials are those metal materials that lack a crystalline shape upon cooling the metal below its melting temperature. Also, as used herein, "Group" refers to the Groups of the Periodic Table of Elements.

The amorphous metal material comprises a first metal (a Group 9, 10, and 11 metals, and combinations comprising at least one of the foregoing first metals), and a non-metal (phosphorous, boron, and combinations comprising at least one of the foregoing non-metals, with phosphorous preferred). The first metals include nickel (Ni), palladium (Pd), platinum (Pt), iridium (Ir), rhodium (Rh), cobalt (Co), copper (Cu), silver (Ag), gold (Au) and combinations comprising at least one of the foregoing first metals. Preferably, the first metal comprises at least one of nickel, silver, palladium, and/or copper, and the non-metal phosphorus; e.g., Pd—Cu—Ni—P, Pd—Ni—P, or Pd—Cu—P, and the like.

The electrode(s) comprising the amorphous material comprise a sufficient amount of the first metal(s) to obtain an amorphous metal material. The electrode(s) may comprise about 10 atomic percent (at %) to about 98 at % of the first metal. All atomic percents set forth herein are based upon the total atoms of the first metal, second metal, and non-metal, unless otherwise specified. Within this range, the first metals are preferably present in an amount of greater than or equal to about 20 at %, with greater than or equal to about 45 at % more preferred. Also within this range, an amount of first metal of less than or equal to about 98 at % is preferred, with less than or equal to about 94 at % more preferred.

Amorphous metal materials may further comprise second metal(s) primarily from Groups 3, 4, and 5. Possible second metals include yttrium (Y), lanthanum (La), titanium (Ti), zirconium (Zr), hafnium (Hf) and niobium (Nb) and combinations comprising at least one of the foregoing second metals. The amorphous metals formed from the second metals may comprise about up to about 60 at % of the combined weight of the second metals in the fired electrode, with about 2 at % to about 60 at % preferred when the second metal(s) are employed. Within this range, the second metal(s) are preferably present in an amount of greater than or equal to about 3 at %, with greater than or equal to about 20 at % more preferred. Also within this range, an amount of second metal of less than or equal to about 55 at % is preferred, with less than or equal to about 50 at % more preferred.

In one embodiment, the non-metal portion of the electrode(s) preferably comprises a sufficient amount of boron (B) and/or phosphorous (P), to fill a sufficient number of the electrode sites available for reaction with elements, such as sulfur, to inhibit sulfur poisoning and alcohol degradation of the electrode. Essentially, sulfur (e.g, $S^{-2}$), and similar elements, in an oxidizing environment, can form a sulfide, for example. As more sulfides form on the original sulfide, a scale builds up on the electrode(s), decreasing their resistivity, and in the case of the fuel level indicator, inhibiting the ability to obtain an accurate level reading. Preferably, greater than or equal to about 80% of the sites are occupied by the non-metal, with greater than or equal to about 90% preferred, and greater than or equal to about 95% more preferred. Essentially, since the amorphous metals do not have grain boundaries, there are no corrosion initiation sites, and sulfide layers will not deposit thereon. The electrode may comprise about 0.5 at % to about 30 at % of the non-metal; e.g, about 47 at % Pd. about 47 at % Ni and about 6 at % P based on the total weight of the fired electrode. Within this range, the electrode preferably comprises greater than or equal to about 0.5 at % of the non-metal, with greater than or equal to about 3.0 at % more preferred, and greater than or equal to about 6.0 at % particularly preferred. Also within this range, the electrode preferably comprises less than or equal to about 25 at % of the non-metal.

A first type of amorphous metal electrode comprising one or more elements from Groups 9, 10, and 11, in combination with phosphorus, is the preferred type. Of this first type, amorphous metal electrode comprising 1 element from Groups 9, 10, and 11, and phosphorus (such as Ni—P, Pd—P, Pt—P, Cu—P, Ag—P, Au—P, and the like) can be employed, with amorphous metal electrode comprising 2 elements from Groups 9, 10, and 11, and phosphorus (such as Ni—Pd—P, Ni—Cu—P, and the like) preferred, and amorphous metal electrode comprising 3 or more elements from Groups 9, 10, and 11, and phosphorus (such as Ni—Ag—Pd—P, and the like) more preferred.

The second type of amorphous metal electrode contains 1 or more elements from Groups 9, 10, and 11 in combination with boron, is preferred over the third type. Of this second type, the amorphous metal electrode can contain 1 element from Groups 9, 10, and 11 and boron (such as Ni—B, Pd—B, Pt—B, Cu—B, Ag—B, Au—B, and the like), with 2 elements from Groups 9, 10, and 11 and boron (such as Ni—Pd—B, Ni—Cu—B, and the like) preferred, and 3 or more elements from Groups 9, 10, and 11 and boron (such as Ni—Ag—Pd—B, and the like) more preferred.

The third type of amorphous metal electrode, which contains 2 or more elements from Groups 9, 10, and 11 in combination with elements from Groups 3, 4, and 5 such as zirconium, and titanium and may optionally include Groups 12 and/or 13 elements such as aluminum and/or zinc. For example, of this third type, the amorphous metal electrode may contain 2 elements from Groups 9, 10, and 11 and 1 element from Group 4 (such as Ni—Cu—Zr, Ni—Ag—Zr, and the like), and/or 2 elements from Groups 9, 10, and 11, and 1 element from Group 13 and 1 element from Group 4 (such as Ni—Cu—Al—Zr, Ni—Ag—Al—Zr, and the like). Of this third type, the amorphous metal electrode may contain 2 elements from Groups 9, 10, and 11 and 1 element from Group 12 (such as Ni—Cu—Zn, Ni—Ag—Zn, and the like), and/or 3 elements from Groups 9, 10, and 11, and 1 element from Group 12 (such as Pd—Ni—Cu—Zn, Ag—Ni—Cu—Zn, and the like). Preferably, the third type of amorphous metal electrode contains 3 or more elements from Groups 9, 10, and 11, and 1 element from Group 13 and 1 element from Group 4 (such as Ni—Cu—Ag—Al—Zr, Ni—Cu—Au—Al—Zr, and the like).

A fourth type or layered material, can also form the amorphous metal material. This layered amorphous metal material comprises layers having a thickness such that, when layered, the layered structure has no long range order such that the material is detected as amorphous, that is, no evidence of crystalline material is detected when examined by X-ray diffraction. Generally, the layers are thin layers (e.g., less than or equal to about 500 micrometers thick). Preferably, the layers have a thickness of less than or equal to about 100 micrometers, with less than or equal to about 50 micrometers more preferred, less than or equal to about 25 micrometers even more preferred. For example, for a 500 micrometer thick electrode, the layers could comprise one layer of crystalline ductile nickel less than or equal to about 8 micrometers thick, then an amorphous layer of metal(s), then a crystalline layer of ductile nickel less than or equal to about 8 micrometers thick, and so on until an electrode of less than or equal to about 75 micrometers thick is formed. Even though some of the material in the 75 micrometers thick layer is crystalline, there is no long range order, so the material is detected as amorphous and is considered to be amorphous. In the layered structure, the layers can comprise layers of a ductile metal (e.g., ductile nickel, copper, cobalt, indium, bismuth, lead, cadmium, tin, and alloys of these metals, and the like), layered with layers of amorphous metals such as $Pd_{40}Ni_{40}Cu_{15}P_5$, and the like, as well as alloys and combinations comprising at least one of the foregoing metals.

Some possible amorphous metal materials include Pd—Cu—Ni—P, Pd—Cu—Ni—Al—P, Pd—Cu—Ni—Zn—P, Pd—Ni—P, Pd—Cu—Ag—P, Cu—Ni—Zn—P, Ni—P, Cu—Ni—Ti—Zr, Cu—Ni—Al—Zr, Cu—Ni—Ag—Zr, Cu—Ni—Al—Ti—Zr, Cu—Ni—Al—Ag—Zr, and Cu—Ni—Zr. Among the foregoing, amorphous electrodes of the form $Pd_wCu_xNi_yP_z$ (PCNP) are preferred. For example, $Pd_{40}Cu_{30}Ni_{10}P_{20}$ and $Pd_{17}Cu_{47}Ni_{12}P_6$ are especially preferred.

The capacitance electrodes may further comprise an over-coating, preferably a thin over-coating, (e.g., a thickness of up to about 60 micrometers), of a material capable of protecting the electrodes. The over-coating is particularly preferred where the fuel's additives create a direct (in phase) electrical conductivity between the capacitance electrodes. Furthermore, the over-coating can protect the capacitance electrodes against reduction by the fuel. The fuel is typically a reducing agent that electrochemically creates reducing activities locally. These reducing activities, in turn, can reduce the weak oxide bonding between the capacitance electrodes and the substrate, and can de-bond the capacitance electrodes from the substrate. The over-coating, however, can protect the capacitance electrodes, while still allowing the flow of AC current through the over-coating. Possible materials for the over-coating include dense glass (e.g., glazing materials, and the like), oxides (e.g., aluminum oxide, and the like), phosphides, borides or combinations comprising at least one of the foregoing materials.

The over-coating, as well as the layers can be formed with various methods such as doctor-blade, cast tape, and the like. The over-coating can also be formed by other methods such as sputtering, screen-printing, painting, spraying, deposition techniques, dipping, and the like. Particularly preferred over-coatings include materials that migrate out of the bulk electrode forming protective coatings such as aluminides and silicides. The over-coating may be formed by migration of metallic aluminum or silicon to the electrode surface forming protective aluminide, silicide or aluminide-silicide coatings.

In addition to the capacitance electrodes, gap, and layers, the sensor may further comprise heater(s), temperature detector(s), and guard electrode(s). The heater(s) serves to evaporate fuel contained within the gap. The temperature detector(s) ensures that the environment to which the sensor is exposed is maintained within a pre-set temperature range and also to monitor the temperature at which the fuel volatilizes. Optionally, the heater(s) and temperature detector(s) can be a single component.

The guard electrode(s), which provides electrostatic shielding between the conductive electrodes and the heater(s) are similarly optional. When the heater(s) are electrically connected to a ground terminal, the ground electrode(s) can be eliminated. The ground electrode(s) decrease the contribution of stray capacitance between the leads to the capacitance as measured by the capacitance measuring circuit (described below).

The heater(s), temperature detector(s), and guard electrode(s) may, individually, comprise various materials such as metals (e.g., precious metals, amorphous metals (as discussed in more detail above)), conducting oxides, and the like, as well as combinations comprising at least one of the foregoing materials. Some possible materials include platinum, palladium, gold, rhodium, iridium, ruthenium, zirconium, yttrium, cerium, aluminum and the like, as well as alloys, oxides, and combinations comprising at least one of the foregoing catalysts. Among the foregoing, platinum, platinum/rhodium, and platinum/palladium are preferred conductor materials. In addition, the conductor material may have interdispersed oxides such as aluminum oxide, silicon oxide, and titanium oxide. The interdispersed oxides may be derived from oxidized intermetallic alloys such as platinum/aluminum, platinum/silicon, and platinum/titanium. The heater(s), temperature detector(s), and guard electrode(s) may comprise the same or different materials.

Figure 3:
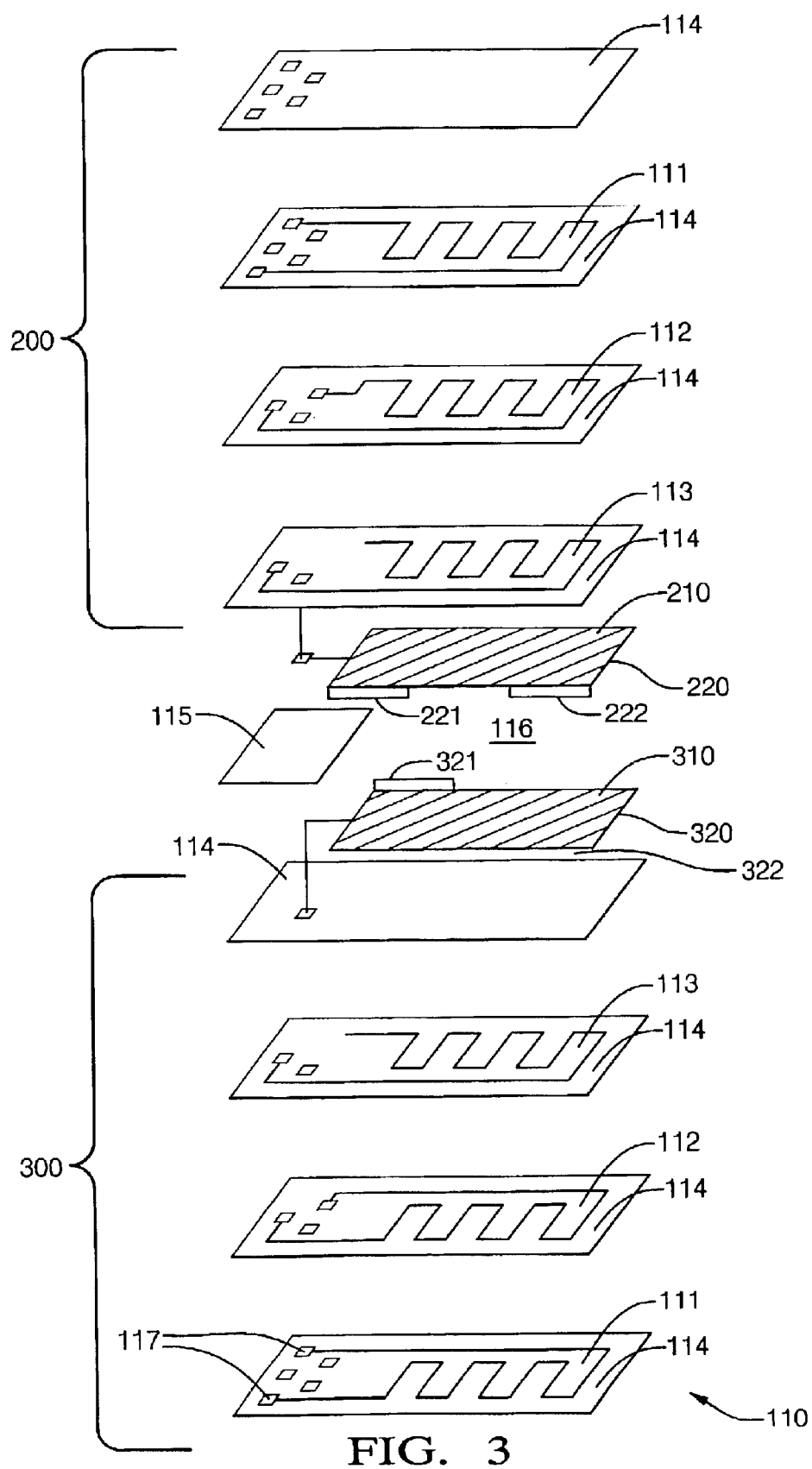
FIG. 3 is a schematic depicting an exemplary embodiment of a sensor.

An exemplary sensor is depicted in FIG. 3. As shown in FIG. 3, the sensor 110 has an upper portion 200 and a lower portion 300. Both the upper portion 200 and the lower portion 300 have a heater 111, a temperature detector 112, and a guard electrode 113 disposed on layers 114. The upper portion 200 has an upper capacitance electrode 210 disposed on an upper layer 220 having a proximal end 221 and a distal end 222. The lower portion 300 has a lower capacitance electrode 310 disposed on a lower layer 320 having a proximal end 321 and a distal end 322. A base insert 115 is disposed between the proximal ends 221, 321 of the upper and lower capacitance electrodes 210, 310 to form a base insert. The rest of the space in the base insert 115 is occupied by a gap (not shown). Via holes 117 are placed on the layers 114 to provide the electrical connections to external controls (not shown).

The sensor disclosed herein may be formed by various methods. An exemplary method is to fabricate the sensor using a ceramic/tape manufacturing technology, which produces a flat-plate device. In this embodiment, the layers and base insert may be formed by forming a slurry comprising ball-milling the materials forming the layers as disclosed above with additional agents, such as, binders plasticizers, surfactants, solvents, and the like, and combinations comprising one of the foregoing. The slurry may then be cast into tapes (e.g., about 150 to about 230 micrometers thick). The capacitor electrodes, guard electrode(s), heater(s), and temperature detector(s) may then be screen printed onto various layers.

The gap insert may be formed in a variety of ways. The gap insert can be a tape, ink, or the like. As a tape, the gap insert can be formed via a method similar to the layers. As an ink, the gap insert can be applied to the desired layer in a manner similar to those described in relation to the electrodes.

Once the layers, the base insert, and the gap insert have been formed, the green (i.e., unsintered) layers can be laid-up; disposed in the desired configuration. Once laid-up, the green layers can be thermally laminated under pressure, cut to individual sensors (if necessary), and then fired in a microwave sintering oven to a sufficient temperature and for a sufficient time to sinter the layers without sintering the base insert (e.g., a temperature of about 850° C. in air for a period of about 15 minutes). After firing, the gap insert can be removed from the sensor, thereby forming the gap. Various extraction techniques can be employed, including physical methods (e.g., ultra-sonic cleaning, pressured air blow gun, pressured liquid jet, hand removing, pick removing, chemical treatment, and the like, as well as combinations comprising at least one of the foregoing methods).

Figure 4:
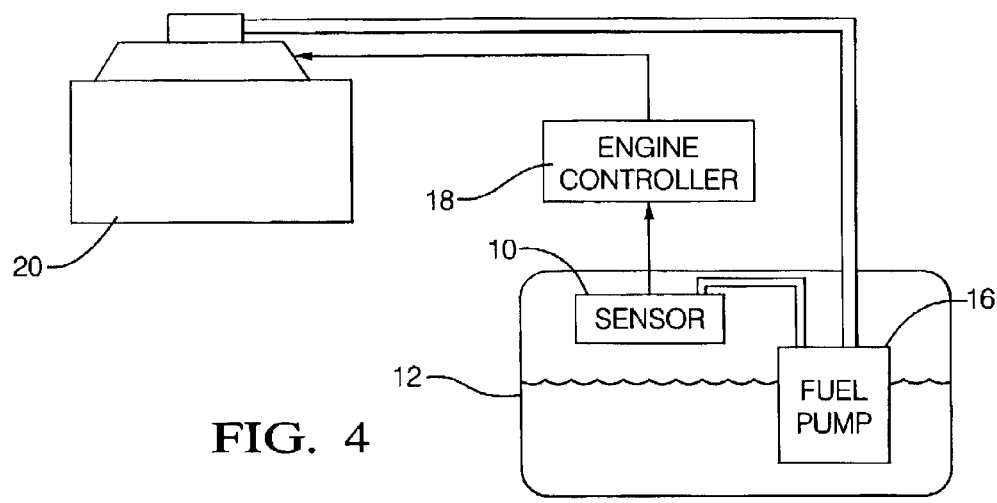
FIG. 4 is a schematic depicting an exemplary apparatus employing the sensor.
Figure 5:
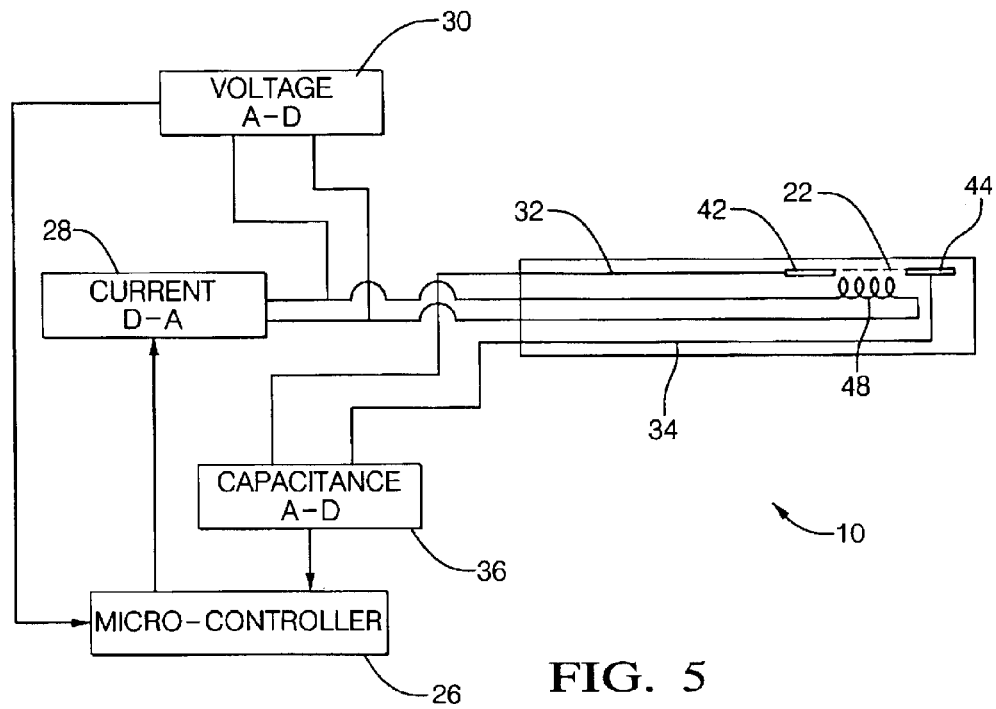
FIG. 5 is a schematic depicting the general path by which the apparatus shown in FIG. 4 may function.

As shown in FIGS. 4 and 5, an exemplary apparatus for the sensor 10 is an engine control system. Specifically, the sensor 10, which can be located in the fuel tank 12 of a vehicle (not shown), receives fuel continuously while the fuel pump 16 is powered on (e.g., during engine operation). In the aspect shown, the fuel sensor 10 receives fuel from the fuel pump 16, but other methods of replenishing the fuel for the sensor 10 are also possible. The sensor 10 collects a sample of the fuel in a gap 22. The gap 22 holds a known volume of fuel, preferably near the top of the volume range that gives an approximately linear capacitance change as a function of fuel volume.

A microcontroller 26 controls the current supplied to heat the heater 48 of the sensor through a digital-to-analog converter 28. The voltage across the heater 48 is measured by a voltage measuring circuit 30, which preferably includes a voltmeter and a converter that converts the signal from analog to digital and provides the result to the microcontroller 26. Additionally, capacitance measuring circuit 36 applies an alternating voltage between capacitance electrodes 42 and 44, through leads 32 and 34, at a selected frequency (e.g., a frequency of about 2 kilohertz (kHz) to about 500 kHz; within this range, a frequency of about 10 kHz is preferred, and a frequency of less then about 100 kHz is also preferred). This frequency is typically based upon a balance of a sufficient frequency to simplify the measurement (e.g., at too high a frequency the measurement is difficult), and costs (as the frequency decreases, the component cost increases).

Application of the alternating voltage creates an electric field that passes into the gap 22. The circuit 36 then measures the resulting capacitance and converts the signal from analog to digital before it is provided to the microcontroller 26. The sensor 10 provides information to the engine controller 18. The engine controller 18 manipulates the data, e.g., compared to a table, and controls the amount of fuel the engine 20 receives from the fuel tank 12 relative to the intake of air upon the next cold start of the engine 20. This control enables reduction in exhaust emissions to a minimum while maintaining vehicle drivability to achieve high customer satisfaction.

The disclosure is further demonstrated by the following examples, which are meant to be illustrative, not limiting.

EXAMPLES

Examples: aluminum oxide tapes were produced by a tape casting method. The sintering agent lithium alumino-silicate ($Li_xAl_xSil_{-x}O_2$), referred to as "LAS glass", was added to lower the firing temperature to 850° C. Tapes without the sintering agents were formed as the gap insert to create the gap space between the layers. The heater, guard and capacitance electrodes were comprised gold ink. To increase the resistance values and to give high PTCR (e.g., 4,000 parts per million (ppm) per ° C.) effect, the temperature detector was made of platinum-aluminum oxide inks. The platinum-aluminum oxide gives higher positive temperature coefficient resistance ratio so that the resolution of the temperature reading can be better. The platinum intermixed with well dispersed nanoscale aluminum oxide prevents a dense electrode from forming, thus making the resistance of the temperature sensor a high resistance. A high resistance electrode at high temperature makes the temperature reading an easier task. The gap had a depth of 0.4 millimeters (mm) and the height was 6 mm. The fired device had a 3.5 ohm as the heater resistance (with gold ink), and 99 ohms as the temperature detector resistance at room temperature (with platinum-aluminum oxide ink). The sensor structure and the layout were the same as the one shown in FIG. 3. The thermal lamination was done at 70° C. and 1.5 kpsi (thousand pounds per square inch) for 10 minutes. After the lamination, the green tile (each containing 12 sensors) was cut into individual sensor pieces. The green sensors were sintered at 850° C. for 20 minutes in air ambient atmosphere. The final thickness of the sensor was 2 mm with a width of 10 mm and a length of 15.4 mm.

Similar sensors were made with a gap depth of 0.2 mm (the rest of the dimensions were the same) with the same materials and techniques. Test results showed the fuel holding between the gap busts out during heating up the sensor for capacitance measurement. Not to be limited by theory, it is believed that could be caused by the bursting of the fuel bubbles formed by the heating within the gap. When the gap depth increases to 0.4 mm, the phenomenon is suppressed.

Driveabilty describes how an engine starts, warms up, and runs. The key characteristic for good driveability is fuel volatility. Fuel volatility should be adjusted for temperatures and altitudes. In cold weather, fuel is blended to vaporize easily, allowing engines to start quickly and run smoothly. In warm weather, fuel is blended to vaporize at higher temperatures, preventing vapor lock and excessive: evaporative emissions. Warm weather gasoline blends used in cold weather causes long start times, warm up delays, hesitations and stalling, e.g. poor driveability. Cold weather gasoline blends used in warm weather cause vapor lock, excessive vapor to liquid ratio, surging, backfiring, loss of power, poor acceleration, excessive emissions, and poor fuel economy.

The driveability index (DI) of a fuel is a measure of total gasoline volatility. The fuel DI is determined from the temperature at which 10% ($T_{10}$), 50% ($T_{50}$) and 90% ($T_{90}$) of the fuel is evaporated. A fuel DI is the sum of $1.5(T_{10})$ and $3.0(T_{50})$ and $1.0(T_{90})$. A high DI (e.g., high octane fuel) indicates a less volatile fuel. Normally gasoline has a DI ranging from about 850 to about 1,300. Summer premium fuel ranges from about 1,200 to about 1,300, while summer regular fuel ranges from about 1,100 to about 1,200. Winter premium fuel ranges from about 1,000 to 1,100, while winter regular fuel ranges from about 850 to about 1,000.

An additional consideration is that some engines are specifically designed with high compression ratios and calibrated to increase engine power using high DI (high octane, low volatility) fuels. Other engines are designed with low compression ratios and calibrated to increase fuel economy and decrease emissions using low DI (low octane, high volatility) fuels. Using high DI (high octane, low volatility) fuels in an engine with a low compression ratio can cause long cold start times, warm up delays, hesitations, die outs, low fuel economy, low acceleration, poor idle quality and high emissions. Poor driveability with high DI fuels is much more common than poor driveability with low DI fuels.

Figure 6:
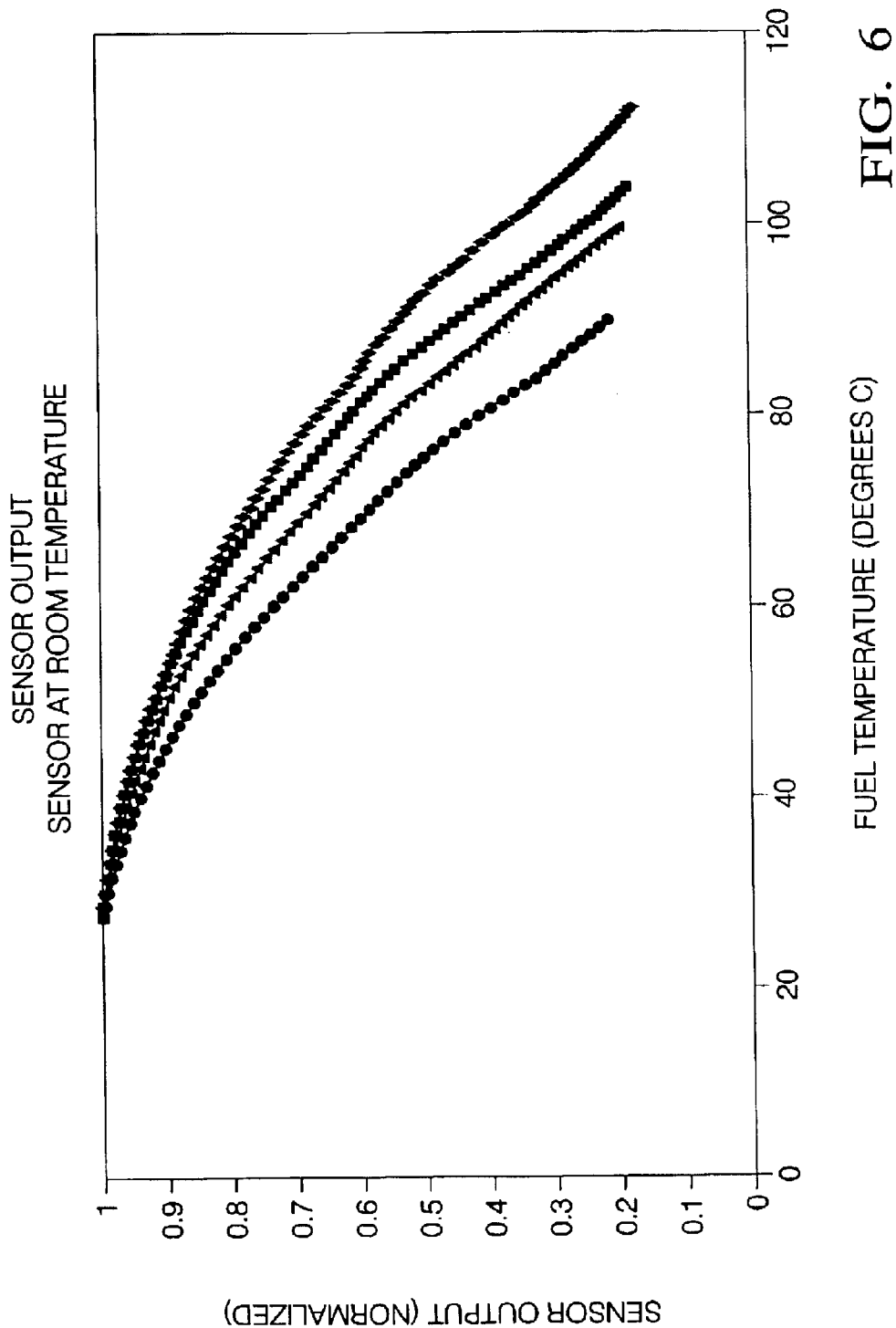
FIG. 6 is a graphical illustration of sensor output versus temperature for four different direct injection fuels.

The described DI sensor does not determine the actual fuel DI, instead the sensor measures capacitance at different temperatures. The curve generated (plotting temperature and sensor output) can then be used to estimate the volatility of the fuel. For example, FIG. 6 shows the sensor output at different temperatures for four different fuels. The horizontal axis is the sample fuel temperature in degrees centigrade, and vertical axis is the normalized measured capacitance. As can be seen from FIG. 6, the sensor output is virtually the same for all four fuels at about 30° C. As the sensor heater increases the fuel temperature, some of the fuel vaporizes and the sensor output, e.g., capacitance, decreases as the fuel volume decreases. In FIG. 6, the fuel with the highest volatility (low DI) reaches a sensor output of about 0.2 at about 90° C. In contrast, the fuel with the lowest volatility (high DI) does not reach a sensor output of about 0.2 until about 110° C.

The sensor provides the capacitance measured at different temperatures to the engine controller. As a result, the measured sensor output may be combined with other sensor outputs. The engine controller compares the sensor inputs to lookup tables. The lookup tables provide control information such as air and fuel adjustments, spark-timing adjustments, valve timing adjustments, and/or exhaust gas recirculation (EGR) adjustments, and the like. These adjustments enable an engine that starts easily when cold, warms up rapidly, and runs smoothly under all conditions, while maximizing good fuel economy and generating low emissions.

The sensor disclosed herein has several advantages over those sensors currently available. First the sensor disclosed herein improves the longevity of the currently available sensors. The sensor is monolithically made and has no joints that can be damaged by thermal cycles or fuel solvent effect. Laboratory thermal cycle test shows the sensor continues the thermal cycles for more than 7 months without any damaging effect. Second, the sensor is formed as a monolithic structure, thereby eliminating unnecessary components and processing steps resulting in a simpler and more easily reproducible manufacturing process, (e.g., the use of glue to hold the layers together is eliminated, thereby eliminating the cost of bonding the parts together). Third, the sensor is sintered at low temperatures (e.g., less than about 900° C.) and eliminates or reduces the need for high temperature materials that usually cost more.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not to be limited to the particular embodiment disclosed as the best mode contemplated for carrying out this invention, but that the invention will include all embodiments falling within the scope of the appended claims.

What is claimed is:

1. A sensor, comprising:
   a monolithic structure comprising
      a first capacitance electrode in fluid communication with a second capacitance electrode through a gap in fluid communication with an exterior of the sensor;
      a first layer disposed on a side of the first capacitance electrode opposite the second capacitance electrode;
      a first heater disposed between a third layer and the first layer;
      a second layer disposed on a side of the second capacitance electrode opposite the first capacitance electrode; and
      a second heater disposed between a fourth layer and the second layer.

2. The sensor of claim 1, further comprising a first guard electrode disposed between the first layer and a fifth layer, with the fifth layer is disposed between the first guard electrode and the third layer, and a second guard electrode disposed between the second layer and a sixth layer, with the sixth layer is disposed between the second guard electrode and the fourth layer.

3. The sensor of claim 2, further comprising a first temperature detector disposed between the fifth layer and a seventh layer, wherein the seventh layer is disposed between the temperature detector and the third layer; and a second temperature detector disposed between the second layer and a eighth layer, wherein the eighth layer is disposed between the temperature detector and the fourth layer.

4. The sensor of claim 1, further comprising a first temperature detector disposed between the first layer and a fifth layer, with the fifth layer is disposed between the first temperature detector and the third layer, and a second temperature detector disposed between the second layer and a sixth layer, with the sixth layer is disposed between the second temperature detector and the fourth layer.

5. The sensor of claim 1, wherein at least one of the first capacitance electrode and the second capacitance electrode comprise an amorphous metal material.

6. The sensor of claim 5, wherein the amorphous metal material further comprises at least one of boron and phosphorous.

7. The sensor of claim 5, wherein the amorphous metal material further comprises a first metal selected from the group consisting of a Group 9 metal, a Group 10 metal, a Group 11 metal, and combinations comprising at least one of the foregoing first metals, and zirconium or at least one of phosphorus and boron.

8. The sensor of claim 7, wherein the amorphous metal material comprises zirconium and further comprising at least one of aluminum and titanium.

9. The sensor of claim 7, wherein the first metal is selected from the group consisting of nickel, palladium, platinum, iridium, rhodium, copper, silver, iron, vanadium, chrome, manganese, cobalt, and combinations comprising at least one of the foregoing first metals.

10. The sensor of claim 9, wherein the first metal is selected from the group consisting of nickel, silver, copper, and combinations comprising at least one of the foregoing first metals.

11. A method for forming a sensor, comprising:
disposing capacitance electrodes and a heater on green layers;
disposing the layers such that the capacitance electrodes are disposed between adjacent green layers and the heat is disposed on a side of a green layer opposite one of the capacitance electrodes;
disposing a gap insert in physical contact with the capacitance electrodes, wherein the gap insert has a higher sintering temperature than the green layers;
sintering the green layers; and
removing the gap insert.

12. The method of claim 11, wherein at least one of the capacitance electrodes comprises an amorphous metal material.

13. The method of claim 12, wherein the amorphous metal material further comprises at least one of boron and phosphorous.

14. The method of claim 12, wherein the amorphous metal material further comprises a first metal selected from the group consisting of a Group 9 metal, a Group 10 metal, a Group 11 metal, and combinations comprising at least one of the foregoing first metals, and zirconium or at least one of phosphorus and boron.

15. The sensor of claim 1, wherein the gap is governed by equation:

$$dh < \frac{\left(\frac{2(A)}{G}\right)}{D}$$

wherein d is a gap width, h is a height of the gap that is vertical to a ground plane, A is a surface energy loss (per unit surface area) created by replacing air with fuel, G is an acceleration of gravity at the surface of the earth, and D is a liquid density of a fuel to be disposed in the gap.

16. The sensor of claim 1, wherein at least one of the capacitance electrodes comprises an over coating, wherein the over coating is selected from the group consisting of glass, aluminum oxide, phosphides, borides, and combinations comprising at least one of the foregoing.

17. The sensor of claim 7, wherein the first metal is present in an amount of about 45 at % to about 94 at %.

18. The sensor of claim 7, wherein the amorphous metal material further comprises a second material selected from the group consisting of yttrium, lanthanum, titanium, hafnium, niobium, and combinations comprising at least one of the foregoing second materials.

19. The sensor of claim 18, wherein the second material is present in an amount of about 20 at % to about 55 at %.

20. The sensor of claim 6, wherein a sufficient amount of boron and/or phosphorus is present to fill greater than or equal to about 90% of electrode sites available for reaction with sulfur.

21. The sensor of claim 1, further comprising a first temperature detector disposed between the first heater and the first capacitance electrode.

22. The sensor of claim 21, further comprising a second temperature detector disposed between the second heater and the second capacitance electrode.

23. A method for forming a sensor, comprising:
disposing a first capacitance electrode on a first green layer;
disposing a second capacitance electrode on a second green layer which is adjacent the first green layer;
disposing a gap insert in physical contact with the capacitance electrodes, wherein the gap insert has a higher sintering temperature than the green layers;
disposing a first heater on a side of the first green layer opposite the first capacitance electrode;
disposing a second heater on a side of the second green layer opposite the second capacitance electrode;
sintering the first green layer and the second green layer; and
removing the gap insert.

24. The method of claim 23, wherein at least one of the first capacitance electrode and the second capacitance electrode comprises an amorphous metal material.

25. The method of claim 24, wherein the amorphous metal material further comprises at least one boron and phosphorous.

26. The method of claim 23, further comprising cofiring the sensor.

27. The method of claim 11, further comprising disposing a temperature detector between the heater and the capacitance electrodes.

28. The method of claim 11, further comprising disposing an overcoating on at least one of the first capacitance electrode and the second capacitance electrode, wherein the over coating is selected from the group consisting of glass, aluminum oxide, phosphides, borides, and combinations comprising at least one of the foregoing.

* * * * *